US009149060B2

(12) United States Patent
Chatel et al.

(10) Patent No.: US 9,149,060 B2
(45) Date of Patent: Oct. 6, 2015

(54) SOLUBLE OAT FLOUR AND METHOD OF MAKING UTILIZING ENZYMES

(71) Applicant: The Quaker Oats Company, Chicago, IL (US)

(72) Inventors: Robert Chatel, Hoffman Estates, IL (US); Yongsoo Chung, Palatine, IL (US); Justin French, Fox River Grove, IL (US)

(73) Assignee: THE QUAKER OAT COMPANY, Plano, TX (US)

( * ) Notice: Subject to any disclaimer, the term of this patent is extended or adjusted under 35 U.S.C. 154(b) by 74 days.

(21) Appl. No.: 14/059,566

(22) Filed: Oct. 22, 2013

(65) Prior Publication Data

US 2014/0050819 A1 Feb. 20, 2014

Related U.S. Application Data

(63) Continuation of application No. 12/666,509, filed as application No. PCT/US2009/060016 on Oct. 8, 2008, now Pat. No. 8,591,970, which is a continuation-in-part of application No. 12/264,399, filed on Nov. 4, 2008, now Pat. No. 8,574,644.

(51) Int. Cl.
| | |
|---|---|
| *A23L 1/105* | (2006.01) |
| *A21D 6/00* | (2006.01) |
| *A23G 9/42* | (2006.01) |
| *A23L 1/00* | (2006.01) |
| *A23L 1/05* | (2006.01) |
| *A23L 1/10* | (2006.01) |
| *A23L 2/02* | (2006.01) |
| *A23L 2/38* | (2006.01) |
| *A23L 2/52* | (2006.01) |

(52) U.S. Cl.
CPC ............... *A23L 1/1055* (2013.01); *A21D 6/00* (2013.01); *A21D 6/003* (2013.01); *A23G 9/42* (2013.01); *A23L 1/0005* (2013.01); *A23L 1/0076* (2013.01); *A23L 1/05* (2013.01); *A23L 1/1041* (2013.01); *A23L 2/02* (2013.01); *A23L 2/38* (2013.01); *A23L 2/52* (2013.01); *C12Y 302/01001* (2013.01); *A23V 2002/00* (2013.01)

(58) Field of Classification Search
CPC ...................................... A23L 1/1055
USPC ......................................... 426/28
See application file for complete search history.

(56) References Cited

U.S. PATENT DOCUMENTS

| | | | |
|---|---|---|---|
| 4,996,063 A | 2/1991 | Inglett | |
| 4,999,298 A | 3/1991 | Wolfe et al. | |
| 5,846,786 A | 12/1998 | Senkeleski et al. | |
| 6,013,289 A | 1/2000 | Blank et al. | |
| 6,054,302 A | 4/2000 | Shi et al. | |
| 6,210,722 B1 | 4/2001 | Wullschleger et al. | |
| 6,723,358 B1 | 4/2004 | van Lengerich | |
| 8,574,644 B2 * | 11/2013 | Chatel et al. | 426/29 |
| 8,591,970 B2 * | 11/2013 | Chatel et al. | 426/28 |
| 2004/0140584 A1 | 7/2004 | Wang et al. | |
| 2004/0151805 A1 | 8/2004 | Gao et al. | |
| 2004/0156971 A1 * | 8/2004 | Wuersch et al. | 426/591 |
| 2004/0258829 A1 | 12/2004 | Zheng et al. | |
| 2006/0013940 A1 | 1/2006 | Mueller et al. | |
| 2007/0104854 A1 | 5/2007 | Foster et al. | |
| 2007/0243301 A1 | 10/2007 | Barnett et al. | |
| 2008/0003340 A1 | 1/2008 | Karwowski et al. | |
| 2008/0260909 A1 | 10/2008 | Chung et al. | |
| 2010/0316765 A1 | 12/2010 | French et al. | |
| 2011/0020523 A1 | 1/2011 | Pereyra et al. | |
| 2012/0082740 A1 | 4/2012 | Collins et al. | |
| 2013/0017300 A1 | 1/2013 | Avila et al. | |
| 2013/0183405 A1 | 7/2013 | Chatel et al. | |
| 2013/0209610 A1 | 8/2013 | Carder et al. | |

FOREIGN PATENT DOCUMENTS

| | | |
|---|---|---|
| EP | 0634106 A1 | 1/1995 |
| EP | 0806434 A1 | 11/1997 |
| EP | 0897673 A2 | 2/1999 |
| EP | 1782699 A2 | 5/2007 |
| JP | 2000004852 | 1/2000 |
| JP | 2002171920 | 6/2002 |
| JP | 2005523331 | 8/2005 |
| WO | 9210106 A1 | 6/1992 |
| WO | 0030457 | 6/2000 |
| WO | 03090557 | 11/2003 |
| WO | 2004086878 A2 | 10/2004 |
| WO | 2006009169 A1 | 1/2006 |
| WO | 2009109703 | 9/2009 |

OTHER PUBLICATIONS

PCT/US14/17288, International Search Report and Written Opinion, dated Jun. 13, 2014.
PCT Application No. PCT/US14/26367, International Search Report and Written Opinion, mailed Sep. 9, 2014.
Japanese Patent Application 2012-108270, Office Action mailed Feb. 4, 2014 (With English Translation).

(Continued)

*Primary Examiner* — Hamid R Badr
(74) *Attorney, Agent, or Firm* — James R. Gourley; Brandon V. Zuniga; Cartens & Cahoon, LLP

(57) ABSTRACT

Producing soluble oat flour by using enzymes to precondition whole oat flour prior to an extrusion (continuous cooking) process.

20 Claims, No Drawings

(56) References Cited

OTHER PUBLICATIONS

Inglett, G.E. et al. 1994. Oat beta-glucan-amylodextrin: Preliminary preparations and biological properties, plant Fd. for Human Nutrition. 45: 53-61.

Office Action for corresponding European Patent Application 09740225.9 dated May 16, 2011.

Linko Y Y et al: "The effect of HTST-extrusion on retention of cereal alpha-amylase activity and on enzymatic hydrolisis of barley starch", Food Processing Systems, Applied Science Publ., UK, Jan. 1, 1980, pages Abstr, 4.2.25, 210-223, XP009127925, ISBN: 978-0-85334-896-2.

Chinese Patent Application 200880025660.8, Office Action dated Aug. 2, 2012.

L.C. Gutkoski et al., "Effect of extrusion process variables on physical and chemical properties of extruded oat products", Plant Foods for Human Nutrition, vol. 54, pp. 315-325, dated Dec. 31, 1999.

Zhang Haodong, "Starch Article Technology", Jilin Science and Technology Press, dated Feb. 29, 2008.

Gualberto, D.G. et al., Effect of extrusion processing on the soluble and insoluble fiber, and phytic acids contents of ceral brans, dated Sep. 28, 1997.

Wang, Ming-chun, et al., Extrusion Technology Applied in the Nutritional Health Foods, College of Food Engineering & Biologic Technology, Tianjin University of Science and Technology, Tianjin 300457, pp. 63-66, dated Aug. 1, 2007, with English Abstract.

Wang Changquing, et al, Study on the Extruding Production Method of Soluble Oats Fiber, vol. 28, No. 2, pp. 45-48, dated Mar. 20, 2002, with English Abstract.

Office Action received for corresponding European Patent Application 09 740 225.9 mailed Oct. 11, 2010.

PCT/US2009/060016, International Search Report, mailed Feb. 8, 2010.

PCT/US2009/060016, Transmittal of International Preliminary Report on Patentability, dated May 19, 2011.

Anonymous: "Ovsena nahradka mlieka", XPOO2561727, URL:htty://web.archive.org/web/20080420075151/http://www.aspsk.sk/ovsene_mlieko.htm>, retrieved from the Internet on Dec. 18, 2009, pp. 1-1, dated Apr. 20, 2008.

Anonymous: "Goldkill Instant Barley Drink", XP002561728, URL:http//web.archive.org/web/2006030300334/goldkill.com/goldkili_instant.php>, retrieved from the Internet on Dec. 28, 2009, pp. 1-2, dated Mar. 3, 2006.

Peter Koelin KGAA: "Kochjule, Hafer-Getrank mit Fruchtsaft", XP002499645, Internet Citation, URL:http://www.koelin.de/downloads/37/Kochjule.pdf>, retrieved from the Internet on Oct. 14, 2008, pp. 1-19, dated Oct. 14, 2008, copy unavailable.

Peter Kolin KGAA: "Kolin Schmeizflocken Dinkel-Hafer", XP002499438, Internet Citation, URL:http://www.koelin.de/produkte/2/103/index.html>, retrieved from the Internet on Oct. 13, 2008, p. 1, dated Oct. 13, 2008.

Peter Kolin KGAA: "kollnFlocken Instant", XP002499437, Internet Citation, URL:http://www.koelin.de/produkte/a/15/index.html>, retrieved from the Internet on Oct. 13, 2008, p. 1, dated Oct. 13, 2008.

Vasanthan, V. et al., "Dextrinization of Starch in Barley Flours With Thermostable Alpha-Amylase by Extrusion Cooking", Starke-Starch, Wiley-VCH Verlag, Weinheim, DE, XP001110714, ISSN: 0038-9056, vol. 53, No. 12, pp. 616-622, dated Dec. 1, 2001 (Abstract Only).

Brenda, The comprehensive Enzyme Information System, BC 3.2.1.1.—alpha amylase; pp. 1 to 297; Retrieved from the Internet: http://www.brenda-enzymes.info/php/result_flat.php4?ecno=3.2.1.1&organism_list=, date unknown.

EP Patent No. EP2205101 (Formerly Application No. EP09740225.9), Notice of Opposition to a European Patent, dated Jul. 10, 2013.

Vasanthan et al., Dextrinization of Starch in Barley Flurs with Thermostable alpha-Amylase by Extrusion Cooking, vol. 53, No. 12, pp. 616-622, dated Dec. 1, 2001.

EP Application 14195125.1-1358, Extended Search Report, dated Jan. 29. 2015.

EP Application 14195095.6-1358 / 2842430, European Search Report, dated Jan. 23, 2015.

EP Application 14195129.3, European Search Report, dated Jan. 26, 2015.

EP Application 14195114.5, Extended European Search Report, dated Jan. 23, 2015.

* cited by examiner

SOLUBLE OAT FLOUR AND METHOD OF MAKING UTILIZING ENZYMES

CROSS REFERENCE OF RELATED APPLICATIONS

This application is a continuation of U.S. Ser. No. 12/666,509 filed Apr. 25, 2011, now allowed, which is a 371 of International PCT/US09/60016, filed Oct. 8, 2008, which is a continuation-in-part of U.S. Ser. No. 12/264,399 filed Nov. 4, 2008, now allowed. The above mentioned applications are incorporated herein by reference in its entirety.

FIELD OF THE INVENTION

The present invention relates generally to soluble oat or barley flour. More specifically, the present invention relates to methods of making soluble oat or barley flour.

BACKGROUND

Oatmeal has for many years been a staple of the human diet due to its health benefits. For example, numerous studies have shown that eating oatmeal on a daily basis can help lower blood cholesterol, reduce risk of heart disease, promote healthy blood flows as well as maintain healthy blood pressure levels. Additionally, oatmeal has high content of complex carbohydrates and fibers, which facilitates slow digestion and stable blood-glucose levels.

With today's hectic lifestyle, consumers are demanding convenience, such as portability and ease of preparation. Consumers desire oatmeal from a variety of food sources including beverages, and convenience foods such as bars, cookies, crackers, smoothies, and the like.

It is desired to prepare a whole oat product that has sufficient soluble fiber to meet the FDA threshold necessary to justify a health claim. For example, a whole oat product must have 0.75 g soluble beta-glucan fiber per serving of food. To prepare an oat beverage that contains at least 0.75 g soluble oat fiber per serving (about 18 g of whole grain oats), highly soluble oat flour must be used. Traditionally, highly soluble flour is prepared using enzymes such as α-amylase. The enzyme-treated oat flour is then drum or spray dried. This method takes place in at least two steps and is traditionally expensive and produces the soluble oat flour in low rates. For example, a slurry batch is prepared of flour (oat) and water (70-90% moisture content). Enzyme (s) are then added to the slurry and held at optimum enzyme reaction conditions followed by enzyme deactivation process. The slurry is then transferred into either a spray or drum drier.

Likewise, barley has become a desired staple of the human diet for health reasons and suitable means to process and prepare barley containing products is desired.

SUMMARY

Aspects of the present invention relate to the use of enzymes to precondition whole oat flour prior to an extrusion (continuous cooking) process. Enzyme-treated oat flour is prepared by combining a whole oat flour starting mixture and a suitable enzyme and then heating the mixture. After a suitable amount of time to begin to break down and hydrolyze the oat or barley flour, the enzyme-treated mixture is then subjected to the extrusion process to continue to break down and hydrolyze the oat or barley flour and further to gelatinize and cook the mixture. Soluble oat or barley flour is thus prepared at low cost and high rates compared to traditional methods.

These and other aspects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

DETAILED DESCRIPTION

The present invention relates to soluble oat or barley flour and a method of producing soluble oat or barley flour using a pre-conditioner and an extruder or other suitable continuous cooker. The process is easier, less expensive, and less time-consuming than prior art processes.

Initially, enzyme-treated oat or barley flour is prepared by combining a whole oat or barley flour starting mixture and a suitable enzyme solution in a pre-conditioner and then heating the mixture. After a suitable amount of time to begin to break down and hydrolyze the oat or barley flour, the enzyme-treated mixture is then subjected to an extrusion process to continue to break down and hydrolyze the oat or barley flour and to gelatinize and cook the mixture.

A starting mixture is prepared containing whole oat or barley flour, granulated sugar, optionally a maltodextrin, and at least one antioxidant.

The whole oat or barley flour is present in an amount of about 50% to about 100by weight of the total weight of the starting composition. In further aspects, the whole oat or barley flour is present in amounts of about 80% to about 100% by weight or about 90% to about 95% by weight.

The sugar can be any suitable sugar known to those skilled in the art. Non-limiting examples of sugars include sucrose, fructose, dextrose, other sugars known in the art, and combinations thereof. Typically, the sugar is present in an amount of 0 to about 15% by weight of the total weight of the starting composition. In further aspects, the sugar is present in amounts of 0 to about 7% by weight.

The maltodextrin may be present in an amount of about 0% to about 15% by weight of the total weight of the starting composition. In further aspects, the maltodextrin is present in amounts of about 3% to about 7% by weight.

The antioxidant may be any suitable antioxidant such as mixed natural tocopherols or artificial antioxidant such as BHT and BHA. The antioxidant is present in an amount from 0.1% to 2% by weight. In further aspects, the antioxidant is present in amounts of about 0.25% to about 0.75% by weight.

The enzyme may be any suitable enzyme to hydrolyze the starch in the oat or barley flour and does not change or adversely affect the beta-glucan that is present in the oat or barley flour. Suitable enzymes include α-amylase. Whether the beta-glucan has changed by the hydrolysis can be determined by any suitable method such as by analyzing the structure of the beta-glucan. This can be done by laser light scattering mass spectroscopy. The enzyme is added to water to form an enzyme water solution. Then the enzyme-water solution is combined with the starting mixture in the pre-conditioner.

The starting mixture and enzyme solution is heated to between about 120° F. and about 200° F., in particular to between about 140° F. and about 180° F. for an effective amount of time to begin to hydrolyze (break down) starch molecules in the oat or barley flour into fractions of polysaccharides.

The starting mixture and enzyme solution may be mixed in a pre-conditioner such as a high speed mixture that permits liquid to be added to free-flowing flour. The output is a free-flowing wetted flour mixture having a moisture content of about 25 to about 40%. The residence time is the time sufficient to obtain the desired result.

The enzyme-treated mixture is subsequently added to an extruder (continuous cooker) to continue to break down and hydrolyze the starch and to gelatinize and cook the starch. The mixture resides in the extruder for a time sufficient to gelatinize and cook the starch, generally at least 1 minute, typically, about 1 to about 1.5 minutes. Generally, the material is heated from an initial inlet temperature to a final exit temperature in order to provide the energy for starch gelatinization.

Starch gelatinization requires water and heat. The gelatinization temperature range for oats is 127° F. to 138° F. (53-59° C.). If the moisture is less than about 60% then higher temperatures are required. Typically the extrusion occurs at barrel temperatures between 140° F. and 250° F. The dough temperatures are approximately 212° F. and 260° F.

Heat may be applied through the extruder barrel wall such as with a jacket around the barrel through which a hot medium like steam, water or oil is circulated, or electric heaters imbedded in the barrel. Heat is also generated within the material by friction as it moves within the extruder. Shear is controlled by the design of the extruder screw(s) and the screw speed. Viscosity is a function of starch structure, temperature, moisture content, fat content and shear.

Low shear is applied to the mixture in the extruder. As the enzyme has preconditioned the starch, high shear is not required for this process. High shear can dextrinize the starch reducing its molecular weight too much. It can also increase the dough temperature excessively, which can overcook it resulting in too much cooked grain flavor.

The process balances limiting the dough temperature to avoid too much cooked grain flavor and to keep the enzyme active and then increasing the temperature to deactivate the enzyme. A low shear extrusion process is characterized relative to high shear extrusion by high moisture and a low shear screw design versus low moisture and a high shear screw design.

Any suitable extruder may be used including suitable single screw or twin screw extruders. Typical, but not limiting, screw speeds are 200-300 rpm.

The resulting product may be pelletized using a forming extruder and dried, typically to about 1.5 to about 10%, for example 6.5 to 8.5%, moisture content. The pellets may be granulated to a Max 85% though a US 30 screen.

The granulated product may be used in beverages such as ready-to-drink beverages, fruit juices, dairy beverages, and carbonated soft drinks, and various food products such as bars, cereals, puddings, smoothies, powdered beverages, cookies, crackers, and the like. The soluble oat or barley flour can be also be used to make soft food products such as ice cream and soft yogurt. This list is not all-inclusive and one skilled in the art would recognize that the soluble oat or barley flour may be added to other beverages and food products in accordance with the invention.

A beverage, for example, contains from about 1% to about 25% soluble oat or barley flour and from about 70% to about 95% total water, typically about 75% to about 90% total water, based on weight of the total drinkable beverage. The balance can contain sweeteners, flavors, fruits and other materials as desired.

The water should be suitable for use in food. The total water may come in part or in whole from other parts of the drinkable food, especially if milk, juices, or other water containing components are used. For instance, the milk may be dairy (e.g. whole, 2%, 1%, or non-fat) or non-dairy (e.g. soy). The milk may also be produced from powdered milk and water.

The beverage may also include a fruit component. The fruit component can include fruit juice, yogurt containing fruit, fruit puree; fresh fruit, fruit preserves, fruit sorbet, fruit sherbet, dried fruit powder, and combinations thereof. Typically, the fruit component has particles sufficiently small that the component may be safely swallowed without chewing. The fruit component and/or an added acidulant can be adjusted to obtain a desired pH, for example a pH of less than about 4.6.

Food products include cereals and ready-to-eat snack bars. A suitable amount of the granulated product is added to the food mixture.

Additional ingredients may be added to the beverage and food products. Such ingredients can include non grain-based ingredients. For example, flavoring agents, coloring agents, sweeteners, salt, as well as vitamins and minerals can be included. In one embodiment of the invention, flavoring agents such as strawberry, chocolate or cinnamon flavor is added to enhance the taste of product. Other fruit flavoring agent may also be useful to provide different tastes to the food product, for example, strawberry, mango and banana and mixtures thereof. Spices, in particular, cinnamon, can be used. In addition, any desired flavor or flavors can be used. Suitable sweeteners—artificial or natural can be added in the food product to provide a desired sweetness. For example, brown sugar, maple sugar or fruit sugar can be used. The non-grain based food component can be added in the range of about 10 to 75 wt % of the total weight of the product.

Other optional ingredients, but are not limited to, salt, hydrocolloids, polysaccharides, thickeners, caffeine, dairy, coffee solids, tea solids, herbs, nutraceutical compounds, electrolytes, vitamins, minerals, amino acids, preservatives, alcohol, colorants, emulsifiers, and oils as known in the art.

The soluble oat or barley flour includes beta glucan soluble fiber, such as beta-1, 3-glucan, beta-1, 6-glucan, or beta-1, 4-glucan or mixtures thereof. In addition to beta glucan naturally present in the oats, beta glucan may also be added as approved by the FDA. In certain embodiments, the oat flour preferably contains at least about 3% to 5% or about 3.7% to 4% beta glucan. In certain embodiments, the oat flour containing liquid product contains 0.1% to about 1.5% beta glucan, or about 0.8% to 1.3% beta glucan. Other amounts of beta glucan are also useful.

As described, the present invention provides both healthy drinkable and edible beverage and food products which are convenient to consume on-the-go, making it especially appealing to consumers with today's hectic lifestyle.

EXAMPLE 1

A flour mix formula for extrusion process.

| Ingredient | % |
| --- | --- |
| Whole oat flour | 89.35 |
| Sugar | 5.00 |
| Maltodextrin | 5.00 |
| Mixed tocopherols | 0.50 |
| α-amylase | 0.15 |
| Total | 100.00 |

Source of α-amylase: Valley Research - Validase ® BAA 1000 L

EXAMPLE 2

A cracker formula is typically made from whole wheat flour or wheat gluten. Instead the formula would be replaced with this hydrolyzed oat flour to improve nutritional benefits (heart health) as well as provide adequate strength to the dough be sheeted and cut into crackers. The formula would include:

| | |
|---|---|
| Modified corn starch | 10.00 |
| Oat flour, Hydrolyzed | 48.00 |
| Oat flakes, old fashioned | 17.00 |
| Brown sugar, free-flowing | 12.00 |
| Malt powder, Briess #10001 | 4.00 |
| Lecithin, powdered, Centrolex F | 2.00 |
| Sodium aluminum phosphate | 0.80 |
| Sodium bicarbonate | 0.70 |
| Salt, flour | 0.60 |
| Corn Oil, with TBHQ, ADM | 5.00 |
| Total | 100.00 |

EXAMPLE 3

A formula for oat ice cream

| Ingredient | % |
|---|---|
| 2% Milk | 87.0 |
| Oat flour, hydrolyzed | 6.5 |
| Sugar | 5.4 |
| Cocoa powder | 0.8 |
| Flavor | 0.2 |
| Modified starch | 0.1 |
| Total | 100.0 |

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A method of producing a whole oat flour having soluble fiber comprising:
    forming a whole oat flour starting mixture comprising about 50 to about 100% whole oat flour, 0 to about 15% granulated sugar, and 0 to about 15% maltodextrin;
    combining the whole oat flour starting mixture and an α-amylase enzyme water solution to form a wetted enzyme starting mixture having a moisture content of about 25 to about 40 wt. %;
    heating the wetted enzyme starting mixture to between about 120° F. and about 200° F.; and
    adding the heated wetted mixture to an extruder and extruding for 1 to 1.5 minutes to produce the whole oat flour having soluble fiber;
    wherein the temperature of the mixture increases in the extruder to a temperature to deactivate the enzyme.

2. The method of claim 1 wherein the whole oat flour starting mixture comprises about 50 to about 95 wt. % whole oat flour.

3. The method of claim 1 wherein the whole oat flour starting mixture comprises about 90 to about 95 wt. % whole oat flour.

4. The method of claim 1 wherein the starting mixture comprises 3% to about 7% by weight of maltodextrin.

5. The method of claim 1 wherein the starting mixture further comprises at least one antioxidant.

6. The method of claim 5 wherein the starting mixture comprises 0.1 to 2 wt. % of the at least one antioxidant.

7. The method of claim 6 wherein the starting mixture comprises 0.25 to 0.75 wt. % of the at least one antioxidant.

8. The method of claim 1 further comprising pelletizing the whole oat flour having soluble fiber.

9. The method of claim 8 further comprising granulating the pelletized whole oat flour having soluble fiber.

10. The method of claim 1 wherein the extruding occurs at a dough temperature of about 212° F. to about 260° F.

11. The method of claim 1 wherein the wetted enzyme starting mixture is heated to 140° F. to about 180° F.

12. The method of claim 1 wherein the extruder has barrel temperature of about 140° F. to about 250° F.

13. The method of claim 1 wherein the extruder has a screw speed of 200-300 rpm.

14. A method for producing a beverage containing a whole oat flour having soluble fiber comprising:
    forming a whole oat flour starting mixture comprising about 50 to about 100% whole oat or barley flour, 0 to about 15% granulated sugar, and 0 to about 15% maltodextrin;
    combining the whole oat flour starting mixture and an α-amylase enzyme water solution to form wetted enzyme starting mixture having a moisture content of about 25 to about 40 wt. %;
    heating the wetted enzyme starting mixture to between about 120° F. and about 200° F.; and
    adding the heated wetted mixture to an extruder and extruding for 1 to 1.5 minutes to form the whole oat flour having soluble fiber;
    wherein the temperature of the mixture increases in the extruder to a temperature to deactivate the enzyme; and
    adding the whole oat flour having soluble fiber to a beverage.

15. The method of claim 14 wherein the beverage is selected from the group consisting of fruit juices, dairy beverages, and carbonated soft drinks.

16. The method of claim 14 further comprising pelletizing the whole oat flour having soluble fiber.

17. The method of claim 14 wherein the extruding occurs at a dough temperature of about 212° F. to about 260° F.

18. The method of claim 14 wherein the wetted enzyme starting mixture is heated to 140° F. to about 180° F.

19. The method of claim 14 wherein the extruder has barrel temperature of about 140° F. to about 250° F.

20. The method of claim 14 wherein the extruder has a screw speed of 200-300 rpm.

* * * * *